(12) United States Patent
Flessland et al.

(10) Patent No.: US 6,667,803 B1
(45) Date of Patent: Dec. 23, 2003

(54) CALIBRATION MODE RECOGNITION AND CALIBRATION ALGORITHM FOR SPECTROPHOTOMETRIC INSTRUMENT

(75) Inventors: Larry D. Flessland, Hutchinson, MN (US); Sergey I. Gritsenko, Hutchinson, MN (US); Mark S. Lewandowski, Hutchinson, MN (US); Dean E. Myers, Stewart, MN (US)

(73) Assignee: Hutchinson Technology, Inc., Hutchinson, MN (US)

( * ) Notice: Subject to any disclaimer, the term of this patent is extended or adjusted under 35 U.S.C. 154(b) by 498 days.

(21) Appl. No.: 09/584,990

(22) Filed: Jun. 1, 2000

Related U.S. Application Data

(60) Provisional application No. 60/137,382, filed on Jun. 3, 1999, provisional application No. 60/137,383, filed on Jun. 3, 1999, and provisional application No. 60/137,390, filed on Jun. 3, 1999.

(51) Int. Cl.[7] .............. G01J 3/42; A61B 5/05
(52) U.S. Cl. ............ 356/319; 356/326; 600/476
(58) Field of Search ............... 356/319, 320, 356/326, 477; 600/476, 309, 310, 300, 473; 250/330, 336.1

(56) References Cited

U.S. PATENT DOCUMENTS

| | | |
|---|---|---|
| 3,874,781 A | 4/1975 | Thiel |
| 4,427,879 A | 1/1984 | Becher et al. |
| 4,684,245 A | 8/1987 | Goldring |

(List continued on next page.)

FOREIGN PATENT DOCUMENTS

| | | |
|---|---|---|
| DE | 44 46 721 A1 | 6/1996 |
| EP | 0 476 596 A1 | 3/1992 |
| EP | 0 800 099 A2 | 10/1997 |
| EP | 0 816 829 A2 | 1/1998 |
| EP | 0 868 881 A1 | 10/1998 |
| EP | 0 290 279 A1 | 11/1998 |
| GB | 1 386 734 | 3/1975 |
| SU | 1 558 643 | 1/1980 |

OTHER PUBLICATIONS

Zotegram, Plastazote Technical Information LD–2, 1 page, 1996.
NIRO 300, Continuous, non–invasive measurement of tissue oxygenation using light, Hamamatsu, Japan (4 pagaes).
INVOS® 3100A Cerebral Oximeter Specifications, Somanetics®, and Somanetics 4100–SSA SomaSensor® (2 pages).

(List continued on next page.)

*Primary Examiner*—Frank G. Font
*Assistant Examiner*—Layla Lauchman
(74) *Attorney, Agent, or Firm*—Faegre & Benson LLP

(57) ABSTRACT

A spectrophotometric instrument including light signal sources, a detector, a processor/controller, a probe and a calibration device. The light signal sources include a source of measurement light signals having measurement light wavelengths and a source of a calibration light signal at a calibration detection wavelength which is different than the measurement light wavelengths. The probe has one or more send fibers coupled to the measurement and calibration light signal sources for transmitting the measurement light signals and the calibration light signal into tissue, and one or more receive fibers for receiving light including the measurement light signals and the calibration light signal. The calibration device is adapted to receive the probe and has an optical filter for transmitting the measurement light signals but not the calibration light signal. The detector is coupled to the receive fibers to generate electrical signals representative of the light received at the receive fibers. The processor/controller is coupled to the detector and initiates a calibration procedure when the calibration light signal is not detected.

21 Claims, 6 Drawing Sheets

U.S. PATENT DOCUMENTS

| | | |
|---|---|---|
| 4,798,440 A | 1/1989 | Hoffer et al. |
| 4,910,539 A | 3/1990 | Mathis et al. |
| 4,998,973 A | 3/1991 | Kikachi |
| 5,140,663 A | 8/1992 | Edwards et al. |
| 5,212,748 A | 5/1993 | Curtiss et al. |
| 5,224,186 A | 6/1993 | Kishimoto et al. |
| 5,224,478 A | 7/1993 | Sakai et al. |
| 5,297,227 A | 3/1994 | Brown et al. |
| 5,339,375 A | 8/1994 | Kerns |
| 5,456,251 A | 10/1995 | Fiddian-Green |
| 5,477,853 A | 12/1995 | Farkas et al. |
| 5,481,634 A | 1/1996 | ANderson et al. |
| 5,584,296 A | 12/1996 | Cui et al. |
| 5,719,977 A | 2/1998 | Lampert et al. |
| 5,774,213 A * | 6/1998 | Trebino et al. ............. 356/320 |
| 5,879,294 A | 3/1999 | Anderson et al. |
| 5,902,246 A | 5/1999 | McHenry et al. |
| 5,923,805 A | 7/1999 | Anderson et al. |
| 6,377,840 B1 * | 4/2002 | Gritsenko et al. .......... 600/476 |

OTHER PUBLICATIONS

PCT International Search Report, PCT/US00/15175 (5 pages).

PCT International Search Report, PCT/US00/15174 (5 pages).

PCT International Search Report, PCT/US00/40086 (5 pages).

* cited by examiner

CALIBRATION MODE RECOGNITION AND CALIBRATION ALGORITHM FOR SPECTROPHOTOMETRIC INSTRUMENT

REFERENCE TO RELATED APPLICATIONS

1. This application claims the benefit of the following U.S. Provisional Applications:

i) Ser. No. 60/137,382 filed on Jun. 3, 1999 and entitled "Calibration Mode Recognition And Calibration Algorithm For Spectrophotometric Instrument."

ii) Ser. No. 60/137,383 filed on Jun. 3, 1999 and entitled "Disposable Tissue Probe Tip."

iii) Ser. No. 60/137,390 filed on Jun. 3, 1999 and entitled "Fiber Optic Light Mixer."

2. Reference is hereby made to the following copending and commonly assigned U.S. Applications which are incorporated herein by reference:

i) Ser. No 09/585,144 filed on Jul. 1, 2000 and entitled "Fiber Optic Light Mixer."

ii) Ser. No. 09/584,862 filed on Jul. 1, 2000 and entitled "Disposable Tissue Probe Tip."

FIELD OF THE INVENTION

The present invention relates generally to the calibration of spectrophotometric instruments. In particular, the invention is a probe, calibration structure and algorithm for calibration of spectrophotometric instruments.

BACKGROUND OF THE INVENTION

Spectrophotometric-type instruments are known and used in a variety of applications. An instrument of this type is, for example, disclosed in the Anderson et al. U.S. Pat. No. 5,879,294. Instruments of this type include an optical probe which is releasably connected to an electronics package. In operation, the probe is positioned on the tissue to be measured or analyzed. The probe is interfaced to the instrument electronics through optical fibers and a probe connector. Light used to measure the characteristics of the tissue is coupled to the probe by send optical fibers. After being transmitted from the tissue-engaging surface of the probe into the tissue being measured, the light will travel through the tissue before being collected at the end of a receive optical fiber. This collected light is then transmitted to the instrument through the probe connector and electronics package connector.

The collected measurement light signals received by the electronics package are transmitted to a detector which produces electrical signals representative of these light signals at each wavelength of interest. A processor/controller then processes these signals to generate data representative of the measured tissue parameter. The measurement can be visually displayed on a display. Algorithms used to compute the tissue parameter data are generally known and described in the Anderson et al. patent.

Calibration procedures are typically performed to enhance the accuracy of the measurements made by the instrument. Methods and devices for calibrating spectrophotometric-type instruments are generally known and disclosed in the Anderson et al. patent. The calibration can, for example, be performed by placing the probe on a calibration device having a housing which is filled with light scattering material. The light scattering material is generally spectrally flat (i.e., reflects all light to the same degree) to provide a reference spectrum. White polyethylene foam such as Plastazote LD45 available from Zotefoams plc. can be used for this purpose.

To obtain an accurate calibration it is important that the-probe be properly positioned on the calibration device during the reference measurement. Inaccurate calibrations will occur when the probe is positioned on the tissue of a patient or otherwise positioned in a manner which enables ambient or other light besides that of the send optical fibers to reach the receive fiber.

There remains a continuing need for improved calibration devices and methods for use with spectrophotometric instruments. Devices and methods which are convenient to use would be especially desirable. Any such devices and methods must be capable of providing accurate calibration procedures.

SUMMARY OF THE INVENTION

The present invention is an instrument, probe and calibration device for conveniently and accurately calibrating a spectrophotometric instrument. One embodiment of the instrument includes light signal sources, a detector, a processor/controller, a probe and a calibration device. The light signal sources include a source of measurement light signals having measurement light wavelengths and a source of a calibration light signal at a calibration detection wavelength which is different than the measurement light wavelengths. The probe has one or more send fibers coupled to the measurement and calibration light signal sources for transmitting the measurement light signals and the calibration light signal into tissue, and one or more receive fibers for receiving light including the measurement light signals and the calibration light signal. The calibration device is adapted to receive the probe and has an optical filter for transmitting the measurement light signals but not the calibration light signal. The detector is coupled to the receive fibers to generate electrical signals representative of the light received at the receive fibers. The processor/controller is coupled to the detector and initiates a calibration procedure when the calibration light signal is not detected.

DETAILED DESCRIPTION OF THE PREFERRED EMBODIMENTS

Figure 1:
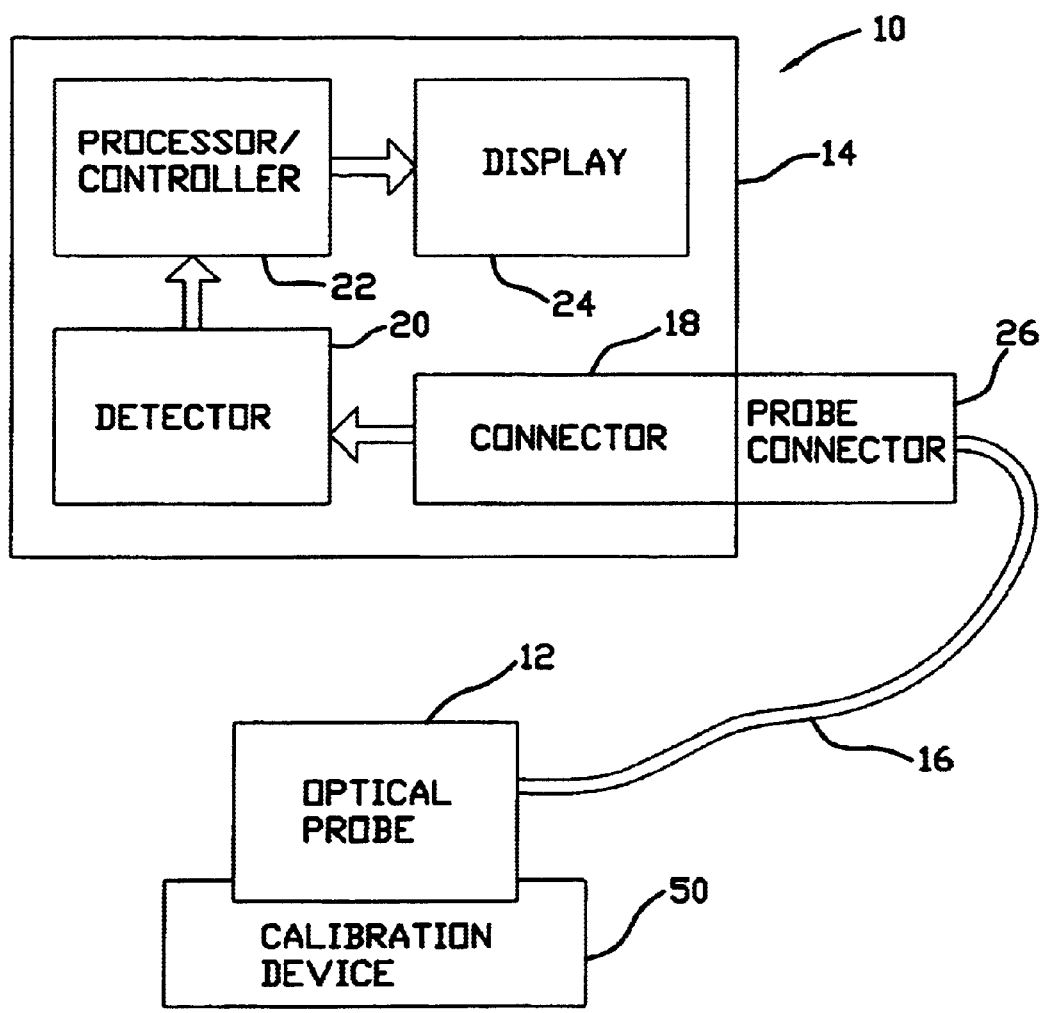
FIG. 1 is block diagram of an instrument useful in the practice of the present invention, along with a probe connector and optical probe connected by optical fibers and a calibration device.
Figure 2:
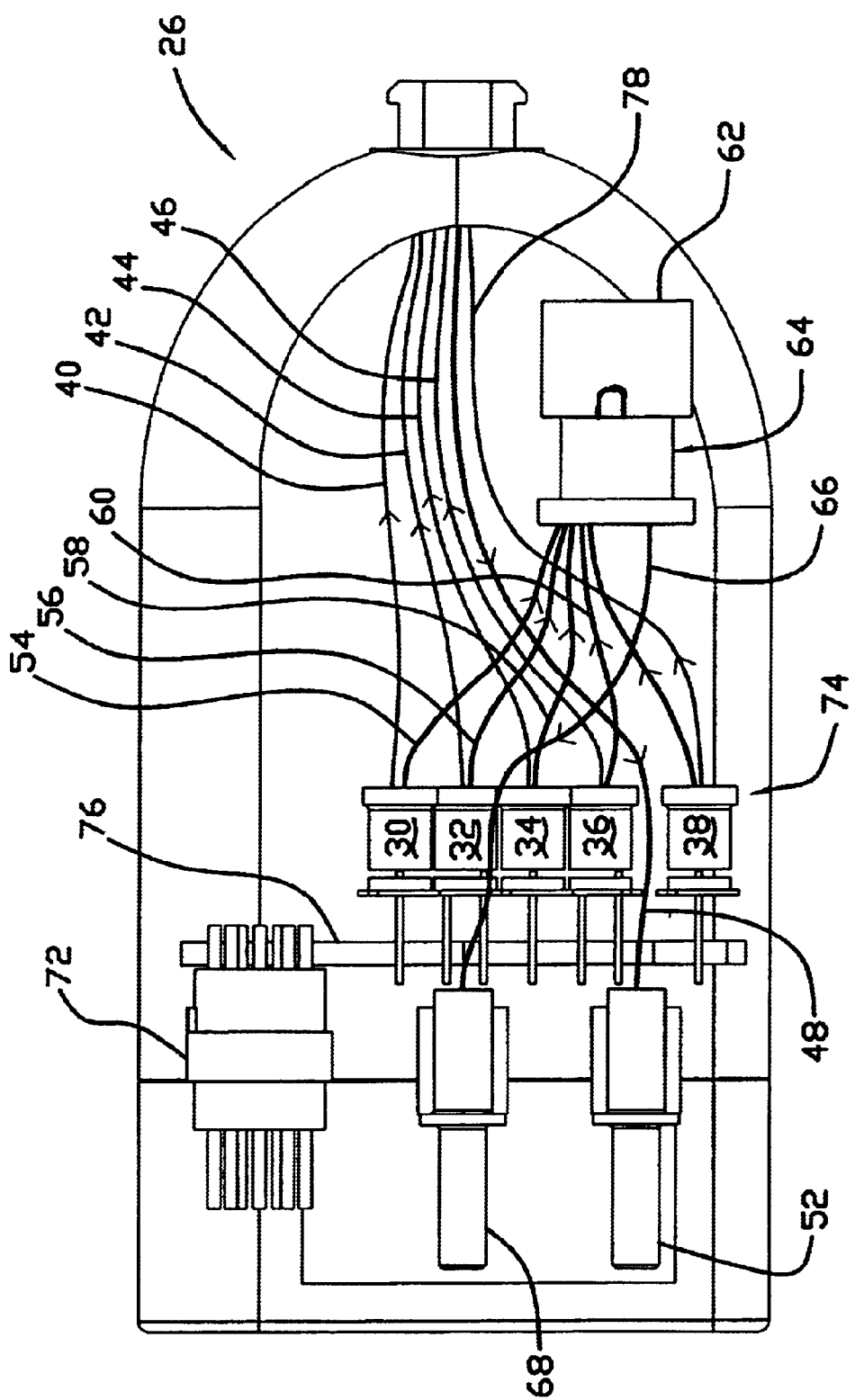
FIG. 2 is a detailed view of the probe connector shown in FIG. 1.

An instrument 10 with which the probe, calibration device and calibration method of the present invention can be used is described generally with reference to FIGS. 1 and 2. As shown, the instrument 10 includes an optical probe 12 which is releasably connected to an electronics package 14 via optical fibers 16. The electronics package 14 includes a connector 18, a detector 20, a processor/controller 22, and a display 24. In operation, the probe 12 is positioned on the tissue to be measured or analyzed. The probe 12 is interfaced to the instrument electronics through the optical fibers 16 and a probe connector 26. The probe connector 26 includes light emitting diodes (LEDs) or other light sources 30, 32, 34, 36, and 38 for generating light at a number of different wavelengths (e.g., 800, 760, 720, 680, and 530 nm, respectively). The light used to measure the characteristics of the tissue is coupled to the probe by send optical fibers 40, 42, 44, and 46. After being transmitted from the tissue-engaging surface of the probe 12 into the tissue being measured, the light will travel through the tissue before being collected at the end of the receive optical fiber 48. This collected light (measurement light signal) is then transmitted to the instrument 14 through the probe connector 26 and electronics package connector 18. A reference light signal corresponding to each of the measurement light signals (i.e., the reference light signals are not transmitted through the tissue) is also transmitted to the electronics package connector 18. Certain aspects of the optical probe 12 are described in greater detail in the above-referenced U.S. Patent Applications entitled "Disposable Tissue Probe Tip" and "Fiber Optic Light Mixer."

The collected measurement light signals and reference light signals received by the electronics package 14 are transmitted to the detector 20 which produces electrical signals representative of these light signals at each wavelength of interest. The processor/controller 22 then processes these signals to generate data representative of the measured tissue parameter (e.g., saturated oxygen level ($StO_2$)). The measurement reading can be visually displayed on the display 24. Algorithms used to compute the tissue parameter data are generally known and described in the Anderson et al. U.S. Pat. No. 5,879,294.

The embodiment of the probe connector 26 illustrated in FIG. 2 has a measurement signal generated within the connector. As shown, the probe connector 26 includes 4 LEDs 30, 32, 34, and 36 for generating the measurement light signals at 680, 720, 760, and 800 nm, respectively. Light signals from each of these LEDs are coupled to the probe 12 by a separate measurement signal send fiber 40, 42, 44, 46. After being transmitted through the tissue being analyzed and collected at the probe 12, the measurement light signal is coupled back to the probe connector 26 by a measurement signal receive fiber 48. The end of the measurement signal receive fiber 48 terminates in the probe connector 26 at a sample ferrule 52 which is adapted to mate with a socket in the connector 18 of the electronics package 14.

A reference light signal is also provided by the probe connector 26. The reference light signal includes a portion of the light from each of the LEDs 30, 32, 34, 36, and has not been transmitted from the probe before being collected. In the embodiment shown in FIG. 2, the reference light signal is collected by reference light signal send optical fibers 54, 56, 58 and 60, which extend respectively from each measurement light signal source LED 30, 32, 34, 36 to a light mixer/attenuator 62 formed by scattering material attached to a reference fiber fixturing ferrule 64. The reference signal send fibers 54, 56, 58, 60 are collected in the fixturing ferrule 64 at the scattering material along with a reference signal receive fiber 66. The reference light received from each LED is mixed at the mixer 62 and transmitted through the reference signal receive fiber 66. The end of the reference signal receive fiber 66 terminates in the probe connector 26 at a reference ferrule 68 which is adapted to mate with a socket in the connector 18 of the electronics package 14. The probe connector 26 also preferably has a 14 pin electrical connector 72 and an optical fiber fixturing ferrule 74 for each of the LED's 30, 32, 34, 36, and 38, each of which are mounted in a PC board 76, along with connector 72. It is to be understood that the arrows on fibers 40, 42, 44, 46 are to indicate "to probe tip" while the arrows on fiber 48 are to indicate "from probe tip."

Figure 3:
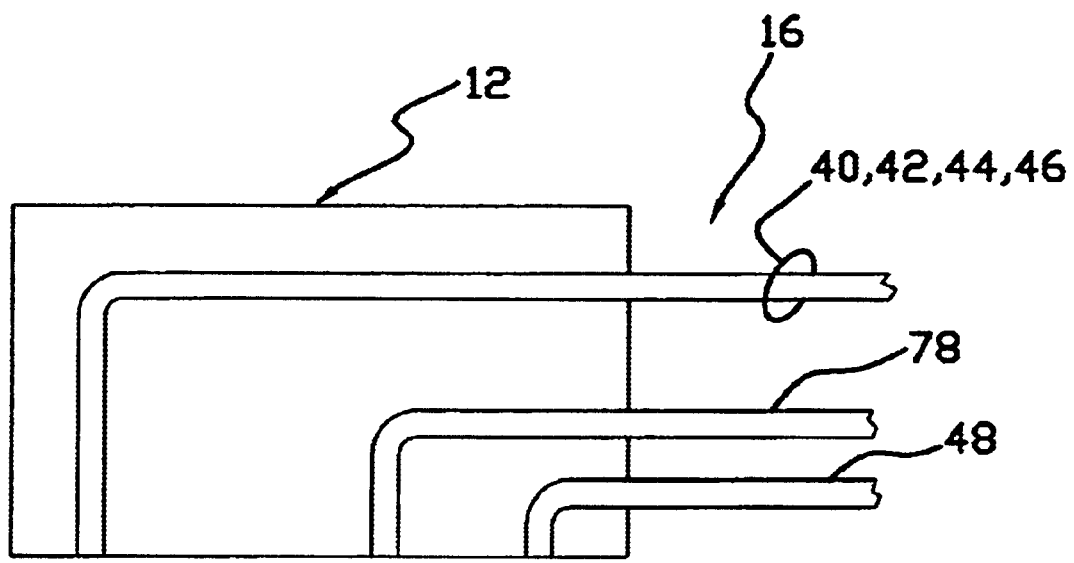
FIG. 3 is a schematic side view of a probe in accordance with the present invention.

LED 38 produces a calibration light signal. The calibration light signal produced by LED 38 is transmitted to the tissue-engaging surface of the probe 12 through a calibration send fiber 78. A schematic diagram of the probe 12 illustrating the measurement signal send fibers 40, 42, 44, 46, measurement signal receive fiber 48 and calibration send fiber 78 is shown in FIG. 3. The calibration light signal produced by LED 38 should be at a wavelength which is separate from, and preferably greater or less than, the range of measurement wavelengths. In the embodiment shown, the calibration light signal is a 530 nm signal.

Figure 4:
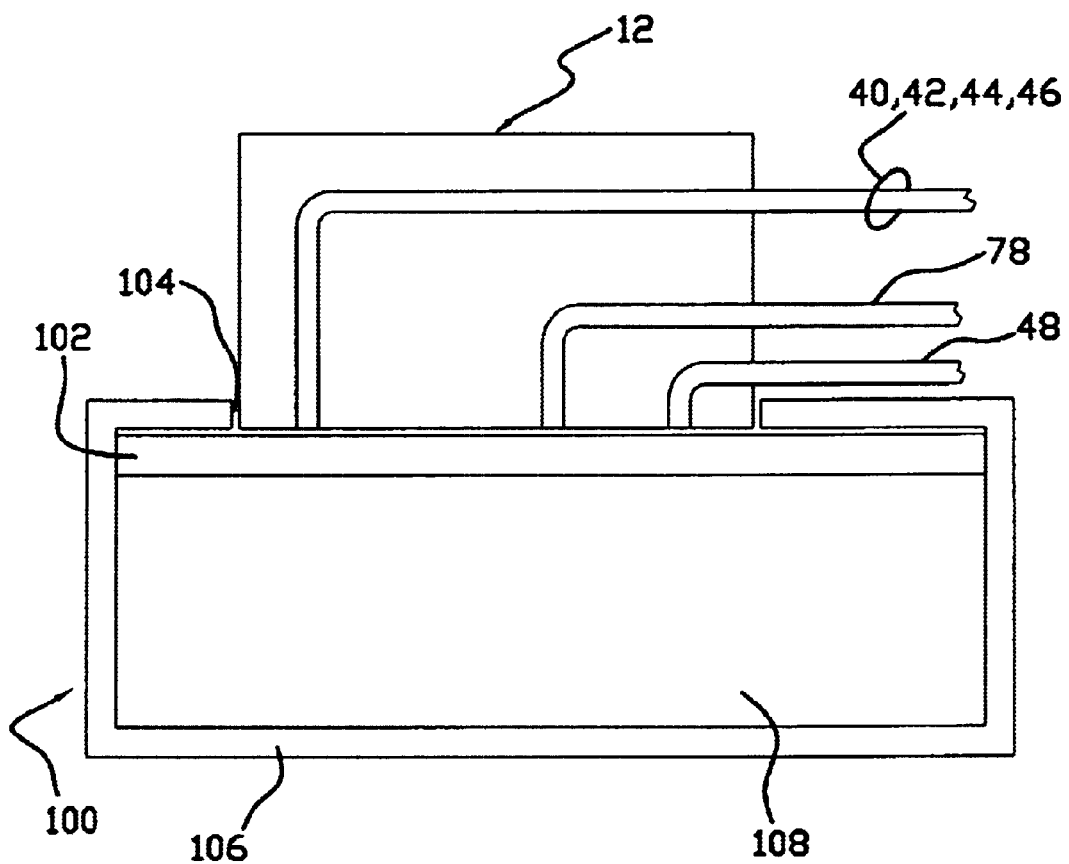
FIG. 4 is a schematic side view of a first embodiment of a calibration device in accordance with the present invention, with the probe shown in FIG. 3 positioned on the device.

A calibration device 100 in accordance with one embodiment of the invention is illustrated schematically in FIG. 4 along with a probe 12. The calibration device 100 includes optical filter material 102 between the opening 104 of the housing 106 at which the probe is received and the interior of the housing with the light-scattering material 108. The calibration optical filter material 102 transmits the measurement light signals (i.e., is optically clear to the measurement signals), but does not significantly transmit the calibration light signal (i.e., is optically opaque to the calibration light signal).

The detector 20 of the electronics package 14 is configured to detect the calibration light signal and to provide electrical signals representative of the calibration light signal (e.g., the presence or absence of a detected calibration light signal) to the processor/controller 22. Since the optical filter material 102 does not transmit the calibration light signal, the receive light signal collected by the receive fiber 48 and transmitted to the electronics package 14 will not contain a significant component at the wavelength of the calibration light signal if the probe 12 is properly positioned on the calibration device 100. The processor/controller 22 is programmed to perform a calibration procedure under these circumstances. If, on the other hand, the probe 12 is positioned on tissue being measured or is not otherwise properly positioned on the calibration device 100, at least portions of the calibration light signal will be present in the receive light signal collected by the receive fiber 48. The processor/controller 22 is programmed in a manner that it will not perform a calibration procedure under these circumstances.

In the embodiment of the instrument and method described above, the scattering material 108 reflects all light wavelengths within the visible and near-infrared wavelength regions (i.e., within the 450–1000 nm wavelength range of the LEDs 30, 32, 34, 36 in the above-described probe connector 26) by substantially the same degree (i.e., is spectrally flat). The optical filter material 102 functions as a bandpass filter and does not significantly transmit light having wavelengths in the range of 450–600 nm. Two distinct light signals are thereby emitted from the probe 12 into the calibration material 102. The first is the primary light signal used to generate the spectroscopic measurement (e.g. 680–800 nm). The second light signal is used only for calibration material 102 recognition purposes and has a discrete wavelength spectrum in the range of 520–540 nm. When the instrument 10 is in the uncalibrated mode, it begins calibration measurements if there is no 520–540 nm light at the same time that there is sufficient detected signal of the primary measurement light at 680–800 nm.

In a preferred embodiment, the light emitted for calibration recognition produces a larger detection signal than the primary measurement light signal when the probe 12 is positioned on materials other than the calibration media 102. Another approach for enhancing the sensitivity of the calibration recognition is to use a recognition light signal source that overlaps the spectra of ambient light (e.g., fluorescent light). When the probe 12 is not on the calibration device 100 the ambient light will add to the detected recognition light signal. The optical filter material 102 should provide a high level and uniformly spectrally flat transmission for the primary measurement light signals. Examples of materials which can be used for signals at the wavelengths described above include Kodak Wrattan 25 available from Eastman Kodak Company of Rochester, N.Y., and Roscolux 25 color filters available from Rosco Laboratories of Port Chester, N.Y. Red Mylar film such as that available from Check-Rite Systems Division of Irvine, Calif., also has the proper spectral properties for the embodiment described above. An alternative to the separate optical filter material 102 is to incorporate red dye having suitable spectral properties into the scattering material foam 108 during its manufacture.

Another advantage of the invention is that the processor/controller 22 can automatically initiate a calibration procedure without having an operator press a button or take other action to start a calibration procedure. The processor/controller 22 can be programmed to initiate a calibration automatically when the probe 12 is positioned on the calibration device 100 (i.e., when the instrument "detects' the optical filter material 102). By automatically detecting and initiating calibration in this manner, a number of calibration error conditions can be avoided. Error conditions of this type can occur when the operator initiates calibration when the calibration material 102 is not present or the operator removes the calibration device 100 before the calibration cycle is completed. Error conditions of these types would detrimentally affect the accuracy of subsequent measurements.

The following is a description of the calibration material recognition process:

1. System monitor (electronics package 14) is powered up.

2. Once a probe 12 is connected to the monitor or package 14, the spectroscopic measurement light (light emitted for tissue absorbance measurements, n=4 wavelength specific LEDs) and the calibration recognition light (emitted for material recognition, n=1 wavelength specific LED) are turned on.

3. If the electronics package 14 has endured the proper warm-up period, the system is ready for calibration.

4. Once the user places the probe 12 on the calibration material 102, four optical sensors (e.g., photomultiplier tubes, not shown) within the electronics package 14 detect the four wavelength specific light intensities emitted from send fibers 40, 42, 44 and 46 which are 25 mm from the receive fiber 48. A fifth optical sensor (e.g., a photo diode, not shown) detects the wavelength specific light emitted for material 102 recognition from the calibration recognition optical fiber 78 spaced 2 mm from the receive fiber 48.

5. If the instrument 10 detects that there is adequate signal at the four photomultiplier tube (PMT) detectors picking up the 25 mm emitted light and that there is inadequate light being detected at the calibration recognition detector (single photodiode) from the 2 mm emitted light, then system reference measurements begin.

6. If any time during the calibration measurement procedure (approx. 20 individual measurements taken and averaged) a significant amount of light is detected at the calibration recognition photodiode detector (light emitted either from the 2 mm spaced optical fiber or from ambient lighting), then an error message is displayed and calibration is halted (e.g., if the user pulls the probe 12 off the material 102 before a complete calibration measurement is captured, then the measurement is restarted once the probe is placed back on the calibration material).

7. Once the calibration procedure is complete, the light emitted for the calibration recognition fiber 78 can be turned off. If the electronics package 14 power is turned off and back on or the probe 12 is disconnected and reconnected then the calibration process is reinitiated.

Figure 5:
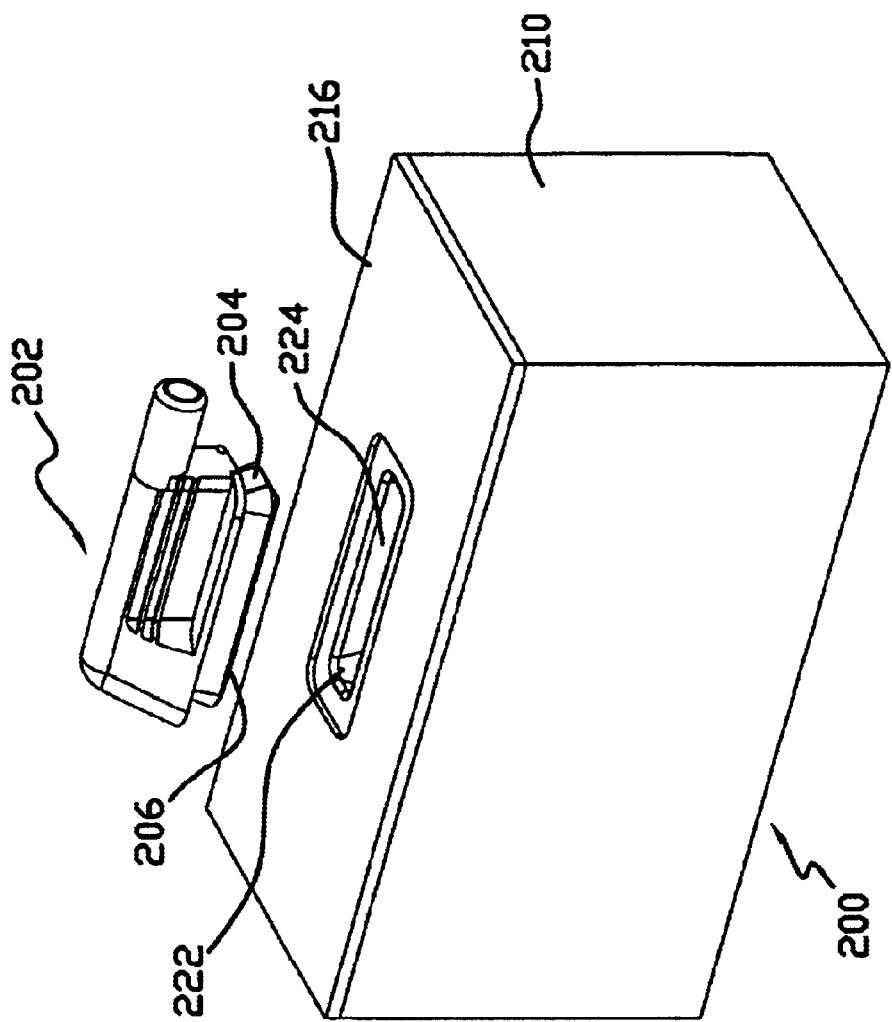
FIG. 5 is an isometric view of a second embodiment of a calibration device in accordance with the present invention, with a probe adapted for use with the calibration device.
Figure 6:
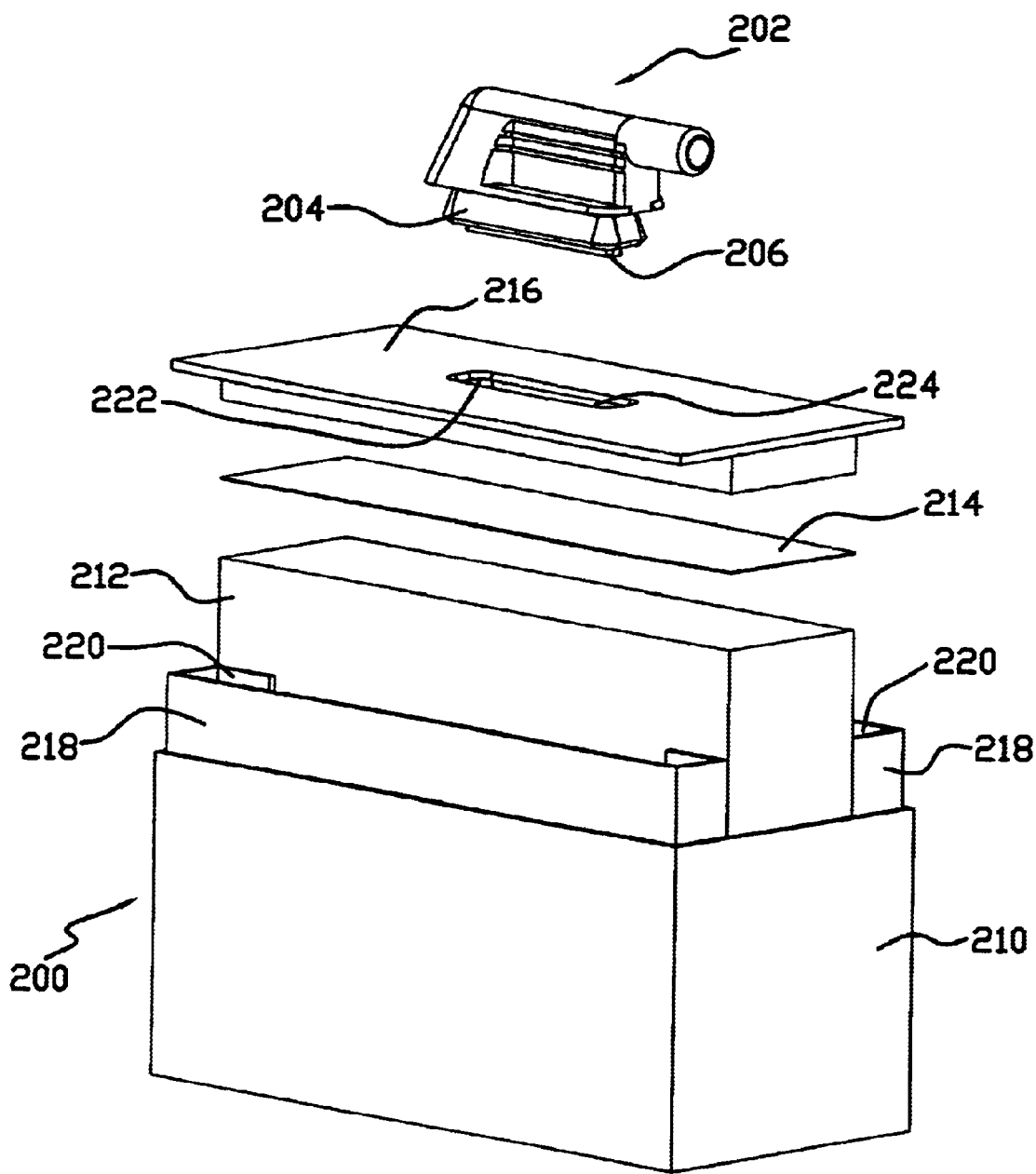
FIG. 6 is an exploded isometric view of the calibration device shown in FIG. 5.

FIGS. 5 and 6 are illustrations of calibration device 200, a second embodiment of a calibration device in accordance with the present invention, and a probe housing 202 which is adapted for use with the calibration device. The housing 202 is described in greater detail in the above-referenced application entitled "Disposable Tissue Probe Tip." Briefly, the housing 202 has a tip-engaging section 204 with an outer surface that extends outwardly with increasing distance toward the tissue-facing surface 206. The tip-engaging section 204 is adapted to enable the probe housing 202 to be conveniently inserted into and removed from a disposable tip (not shown).

Calibration device 200 includes a housing 210 for receiving light-scattering material 212, optical filter material 214 and cover 216. Light-scattering material 212, which can be the same white foam materials as the light-scattering material 108 of the calibration device 100 described above (e.g., white Plastazote), is supported within the housing 210 by supports 218 to maintain voids or air spaces 220 between the major surfaces of the material and the interior of the housing. In one embodiment the light-scattering material 212 is about 2.5 cm in width, 7.6 cm in height and 8.9–11.4 cm in length. The air spaces 220 can have the same height and length as the light-scattering material 212, and a width of about 0.2 cm. The housing 210 and cover 222 can be formed from opaque material such as black plastic. Optical filter material 214 can be formed from the same materials as the material 102 of the calibration device 100 described above.

Cover 216 includes an access opening 222 which is sized to receive the tip-engaging section 204 of the probe housing 202. The opening 222 is lined with resilient light-tight seal 224 which engages the tip-engaging section 204 of the probe housing 202 when the probe housing is inserted into the opening.

Calibration device 200 functions in a manner similar to that of the device 100 described above. However, the size of the light-scattering material 212 and the air spaces 220 reduce the effects of spectral bias related to the spacing between the send and receive fibers (not visible) in the probe 202. Spectral bias of these types can occur when emitted measurement light signals significantly penetrate the light-scattering material 212 and reaches the material boundary of the housing 210.

The present invention offers important advantages. In particular, it efficiently provides accurate calibration operations. Errors which can otherwise be caused by poor-quality coupling between the probe and calibration device are automatically identified and reduced.

Although the invention has been described in connection with a plurality of discrete and relatively narrow bandwidth light signal sources, those skilled in the art will recognize that it can be implemented with a broad bandwidth light signal source as well. The calibration light signal could also be mixed with the measurement light signals. Furthermore, although described in connection with a calibration device recognition application, the invention can be used to determine probe positions in other applications as well. For example, using an appropriate wavelength of light (e.g., blue or UV), the instrument can be adapted to recognize whether the probe is properly positioned on or off tissue being analyzed.

What is claimed is:

1. A spectrophotometric instrument including:
   a source of measurement light signals having measurement light wavelengths;
   a source of a calibration light signal at a calibration detection wavelength which is different than the measurement light wavelengths;
   a probe having:
      one or more send fibers coupled to the measurement and calibration light signal sources for transmitting the measurement light signals and the calibration light signal into tissue, and
      one or more receive fibers for receiving light from tissue including the measurement light signals and the calibration light signal;
   a calibration device adapted for receiving the probe and having an optical filter for transmitting the measurement light signals but not the calibration light signal;
   a detector coupled to the receive fibers for generating electrical signals representative of the light received at the receive fibers; and
   a processor/controller coupled to the detector for initiating a calibration procedure when the: calibration light signal is not detected.

2. The instrument of claim 1 wherein the processor/controller automatically initiates the calibration procedure when the calibration light signal is not detected.

3. The instrument of claim 1 wherein the processor/controller initiates the calibration procedure only when the calibration light signal is not detected.

4. A spectrophotometric instrument including:
   a source of measurement light signals having measurement light wavelengths;
   a source of a calibration light signal at a calibration detection wavelength which is different than the measurement light wavelengths;
   a probe having:
      one or more send fibers coupled to the measurement and calibration light signal sources for transmitting the measurement light signals and the calibration light signal into tissue, and
      one or more receive fibers for receiving light from tissue including the measurement light signals and the calibration light signal;
   a calibration device adapted for receiving the probe and having an optical filter for transmitting the measurement light signals but not the calibration light signal;
   a detector coupled to the receive fibers for generating electrical signals representative of the light received at the receive fibers; and
   a processor/controller coupled to the detector for inhibiting a calibration procedure when the calibration light signal is detected.

5. The instrument of claim 4 wherein the calibration detection wavelength is shorter than the measurement light wavelengths.

6. The instrument of claim 4 wherein the optical filter is a bandpass filter.

7. The instrument of claim 4 wherein the probe has separate measurement light signal send fibers and calibration light signal send fiber.

8. The instrument of claim 7 wherein the end of the calibration light signal is closer to the end of the receive fiber than to the end of the measurement light signal send fibers.

9. A probe for use with a spectrophotometric instrument, including:
   a probe having a tissue-facing surface;
   one or more measurement emitters for emitting send measurement light signals from the tissue-facing surface;
   one or more calibration emitters for emitting a calibration recognition light signal from the tissue-facing surface; and
   one or more receivers for receiving receive measurement light signals and receive calibration light signals at the tissue-facing surface.

10. The probe of claim 9 wherein the measurement emitters, receivers and calibration emitters include optical fibers.

11. A spectrophotometric instrument, including:
    a receive terminal for receiving a receive measurement light signal;
    a calibration terminal for receiving a calibration recognition light signal; and
    a processor/controller for performing calibration procedures as a function of the measurement light signal and the calibration recognition light signal.

12. The instrument of claim 11 wherein the processor/controller performs calibration procedures when the calibration recognition light signal is not received.

13. The instrument of claim 11 wherein the processor/controller inhibits the performance of calibration procedures when the calibration recognition light signal is received.

14. A calibration device for use in connection with a spectrophotometric instrument having an optical probe of the type emitting send measurement light signals and calibration recognition light signals and receiving receive measurement light signals, including:
    a housing including an opening for receiving the optical probe;
    spectrally flat light-scattering material within the housing;
    a filter between the probe opening and light-scattering material, the material relatively transparent to the send measurement light signals and the receive measurement light signal, and relatively opaque to the calibration recognition light signals.

15. A spectrophotometric instrument, including:
    a source of measurement light signals having measurement light wavelengths;
    a source of a probe position recognition light signal at a recognition wavelength which is different than the measurement light wavelengths;
    a probe for coupling the measurement light signals and the probe position recognition light signal into tissue, and for receiving the measurement light signals and the probe position recognition light signals from the tissue;
    a detector coupled to the probe for generating electrical signals representative of the light received at the probe; and
    a processor/controller coupled to the detector for determining the position of the probe with respect to an object as a function of the detected recognition light signal.

16. A method of calibrating a spectrophotometric instrument, comprising the steps of:

illuminating a target with first and second light signals;

detecting a return light signal from the target;

initiating a calibration procedure if a predetermined component of the first light signal is not present in the return light signal; and producing an instrument readout signal otherwise.

17. The method of claim 16, comprising the further step of:

providing a target that does not allow the first light signal to be detected as part of the return light signal.

18. The method of claim 16, wherein a primary wavelength of the first light signal is shorter than a primary wavelength of the second light signal.

19. The method of claim 16, wherein the second light signal is created from plural light sources having different primary wavelengths.

20. The method of claim 17, wherein a primary wavelength of the first light signal is shorter than a shortest primary wavelength of the second light signal.

21. A spectrophotometric instrument operable with a source of calibration light signal including:

a source of measurement light signals having measurement light wavelengths;

a probe having:

one or more send fibers coupled to the measurement light signal sources for transmitting the measurement light signals, and one or more receive fibers for receiving light from a target;

a detector coupled to the receive fibers for generating electrical signals representative of the light received at the receive fibers; and a processor/controller coupled to the detector for initiating a calibration procedure when the calibration light signal is not detected.

* * * * *